US010595795B2

(12) United States Patent
Pfister

(10) Patent No.: US 10,595,795 B2
(45) Date of Patent: Mar. 24, 2020

(54) ANGIOGRAPHIC EXAMINATION METHOD FOR OVERLAYING VIRTUAL VASCULAR PROJECTION IMAGES WITH MEDICAL INSTRUMENT PROJECTION IMAGES BASED ON PROJECTION MATRIX

(71) Applicant: Marcus Pfister, Bubenreuth (DE)

(72) Inventor: Marcus Pfister, Bubenreuth (DE)

(73) Assignee: Siemens Aktiengesellschaft, München (DE)

(*) Notice: Subject to any disclaimer, the term of this patent is extended or adjusted under 35 U.S.C. 154(b) by 1455 days.

(21) Appl. No.: 14/503,356

(22) Filed: Sep. 30, 2014

(65) Prior Publication Data

US 2015/0094567 A1  Apr. 2, 2015

(30) Foreign Application Priority Data

Sep. 30, 2013 (DE) .......................... 10 2013 219 737

(51) Int. Cl.
*A61B 6/12* (2006.01)
*A61B 6/03* (2006.01)
(Continued)

(52) U.S. Cl.
CPC .................. *A61B 6/12* (2013.01); *A61B 6/03* (2013.01); *A61B 6/4441* (2013.01); *A61B 6/463* (2013.01);
(Continued)

(58) Field of Classification Search
None
See application file for complete search history.

(56) References Cited

U.S. PATENT DOCUMENTS 6,317,621 B1 * 11/2001 Graumann ............... A61B 6/12
600/424
6,720,966 B2 * 4/2004 Barth .................... G06T 11/005
250/363.04
(Continued)

FOREIGN PATENT DOCUMENTS

DE  102005028746 A1  12/2006
DE  102006001884 A1   7/2007
(Continued)

OTHER PUBLICATIONS

Hoffmann et al 2012_Semi-automatic Catheter Reconstruction from Two Views.*
(Continued)

*Primary Examiner* — Serkan Akar
(74) *Attorney, Agent, or Firm* — Lempia Summerfield Katz LLC

(57) ABSTRACT

An angiographic examination method for depicting a target region as an examination object using an angiography system includes capturing a volume data set of the target region with the examination object, registering the volume data set to a C-arm, and extracting information about an assumed course of the examination object in the volume data set. The method also includes generating a 2D projection image of a medical instrument in the target region, 2D/3D merging the 2D projection image and the registered volume data set for generating a 2D overlay image, and detecting the instrument in the 2D overlay image with a first projection matrix. The method includes generating a virtual 2D projection using a virtual projection matrix, 3D reconstructing the instrument, and distorting at least part of the reference image such that the current and the assumed course of vessels are made to be congruent.

20 Claims, 11 Drawing Sheets

(51) Int. Cl.
*G06T 7/30* (2017.01)
*A61B 6/00* (2006.01)

(52) U.S. Cl.
CPC ............ *A61B 6/504* (2013.01); *A61B 6/5235* (2013.01); *G06T 7/30* (2017.01); *A61B 6/4458* (2013.01); *A61B 6/481* (2013.01); *A61B 6/487* (2013.01); *A61B 6/5223* (2013.01); *G06T 2207/10081* (2013.01); *G06T 2207/30101* (2013.01)

(56) References Cited

U.S. PATENT DOCUMENTS

| | | | |
|---|---|---|---|
| 7,500,784 | B2 | 3/2009 | Grebner et al. |
| 7,519,415 | B2 * | 4/2009 | Mitschke ................ A61B 6/02 600/424 |
| 8,457,375 | B2 * | 6/2013 | Rieber .................. A61B 90/37 345/629 |
| 2001/0041838 | A1 * | 11/2001 | Holupka .................. A61B 8/08 600/439 |
| 2003/0220555 | A1 * | 11/2003 | Heigl ...................... A61B 6/12 600/407 |
| 2006/0285638 | A1 | 12/2006 | Boese et al. |
| 2007/0197897 | A1 | 8/2007 | Diez |
| 2008/0181367 | A1 * | 7/2008 | Heigl ..................... A61B 6/032 378/207 |
| 2009/0088830 | A1 * | 4/2009 | Mohamed ................ A61F 2/91 623/1.11 |
| 2011/0235876 | A1 | 9/2011 | Pfister et al. |
| 2012/0238871 | A1 | 9/2012 | Pfister |
| 2014/0180063 | A1 * | 6/2014 | Zhao ..................... A61B 5/066 600/424 |
| 2015/0237359 | A1 * | 8/2015 | Alshin .................. H04N 19/43 375/240.16 |

FOREIGN PATENT DOCUMENTS

| | | |
|---|---|---|
| DE | 102007051479 B4 | 4/2010 |
| DE | 102010012621 A1 | 9/2011 |
| DE | 102011005777 A1 | 9/2012 |

OTHER PUBLICATIONS

Bender et al Reconstruction of 3D Catheter Paths from 2D X-ray Projections.*
Guyot et al 2013_Non-Rigid 2D-3D Registration Using Anisotropic Error Ellipsoids to Account for Projection Uncertainties during Aortic Surgery.*
German Office Action for German Application No. 10 2013 219 737.3, dated Feb. 25, 2014.

* cited by examiner

ANGIOGRAPHIC EXAMINATION METHOD FOR OVERLAYING VIRTUAL VASCULAR PROJECTION IMAGES WITH MEDICAL INSTRUMENT PROJECTION IMAGES BASED ON PROJECTION MATRIX

This application claims the benefit of DE 10 2013 219 737.3, filed on Sep. 30, 2013, which is hereby incorporated by reference in its entirety.

BACKGROUND

The present embodiments relate to an angiographic examination method for depicting a target region inside a patient with a vascular system as an examination object.

An angiography system for the performance of an angiographic examination method is known, for example, from U.S. Pat. No. 7,500,784 B2, which is explained below based on FIG. 1.

FIG. 1 shows a monoplanar X-ray system depicted as an example with a C-arm 2 held by a stand 1 in the form of a six-axis industrial or articulated robot. The X-ray system includes an X-ray source (e.g., an X-ray emitter 3 with X-ray tube and collimator) and an X-ray image detector 4 being attached to ends of the C-arm 2 as an image recording unit.

Using the articulated robot known, for example, from U.S. Pat. No. 7,500,784 B2, which may have six axes of rotation and thus six degrees of freedom, the C-arm 2 may be displaced spatially, as required, being rotated, for example, about a center of rotation between the X-ray emitter 3 and the X-ray image detector 4. The angiographic X-ray system 1 to 4 is rotatable, for example, about centers of rotation and axes of rotation at the C-arm plane of the X-ray image detector 4 (e.g., about the center of the X-ray image detector 4) and about axes of rotation intersecting the center of the X-ray image detector 4.

The known articulated robot has a baseframe that, for example, is permanently mounted on a floor. To this, a carousel is rotatably attached about a first axis of rotation. Attached to the carousel so as to pivot about a second axis of rotation is a robot rocker arm, to which a robot arm that may rotate about a third axis of rotation is fixed. A robot hand is attached at the end of the robot arm, so as to rotate about a fourth axis of rotation. The robot hand has a fixing element for the C-arm 2, which may pivot about a fifth axis of rotation and may rotate about a sixth axis of rotation extending perpendicular thereto.

The implementation of the X-ray diagnostic device is not dependent on the industrial robot. Normal C-arm devices may also be used.

The X-ray image detector 4 may be a rectangular or square, flat semiconductor detector that may be made of amorphous silicon (a-Si). Integrating and possibly counting CMOS detectors may also be used, however.

Located in the beam path of the X-ray emitter 3 on a tabletop 5 of a patient positioning couch is a patient 6 to be examined as an examination object. On the X-ray diagnostic device, a system control unit 7 is connected to an image system 8 that receives and processes the image signals from the X-ray image detector 4 (e.g., operating elements are not shown). The X-ray images may be viewed on displays of a monitor bracket 9. The monitor bracket 9 may be held by a ceiling-mounted support system 10 with a cantilever arm and a lowerable support arm, may travel lengthwise, pivot and rotate, and is height-adjustable. Also provided in the system control unit 7 is an apparatus 11, the function of which is further described below.

Instead of the X-ray system illustrated by way of example in FIG. 1 with the stand 1 in the form of the six-axis industrial or articulated robot, the angiographic X-ray system may also have a normal ceiling- or floor-mounted bracket for the C-arm 2.

Instead of the C-arm 2 shown by way of example, the angiographic X-ray system may also have separate ceiling- and/or floor-mounted brackets for the X-ray emitter 3 and the X-ray image detector 4, which, for example, are electronically fixedly coupled.

The X-ray emitter 3 emits a beam of radiation 12 originating from a beam focus of an X-ray radiation source of the X-ray emitter 3. The beam strikes the X-ray image detector 4. If 3D data sets are to be generated in accordance with the DynaCT method (e.g., a method for rotational angiography), the rotatably mounted C-arm 2 with X-ray emitter 3 and X-ray image detector 4 is rotated such that, as shown schematically in FIG. 2 by the aerial view of the axis of rotation, the X-ray emitter 3 (e.g., represented by a beam focus) and the X-ray image detector 4 move in an orbit 14 about an object 13 to be examined that is located in the beam path of the X-ray emitter 3. In order to generate a 3D data set or volume data set, the orbit 14 may be full or partial.

In accordance with the DynaCT method, the C-arm 2 with X-ray emitter 3 and X-ray image detector 4 may move by an angular range of at least 180° (e.g., 180° plus fan angle), and records projection images in rapid succession from various projections. The reconstruction may be performed using just one section of this recorded data.

The object 13 to be examined may, for example, be an animal body, a human body, or a phantom body.

The X-ray emitter 3 and the X-ray image detector 4 each move about the object 13 such that the X-ray emitter 3 and the X-ray image detector 4 are positioned at opposite sides of the object 13.

In normal radiography or fluoroscopy using an X-ray diagnostic device of this type, the medical 2D data of the X-ray image detector 4 may be buffered in the image system 8 and subsequently displayed on the monitor bracket 10.

Angiography systems of this type are used in the field of fluoroscopy-controlled, interventional repairs to abdominal aortic aneurysms.

An abdominal aortic aneurysm (AAA) or aneurysma verum aortae abdominalis is a vascular dilatation on the abdominal aorta, a widening of the abdominal aorta below the branching of the renal arteries in the anterior/posterior diameter of over 30 mm. This is treated by using a stent graft. By way of both groins, guide wires and catheters are inserted into the aorta. Via this, one or more stent grafts (i.e., composite vascular stents) are inserted (see FIG. 3), as shown, for example, in Cardiology Today, January 2011, page 36.

The purpose of using these stent grafts is to position the landing zone of the vascular prosthesis as far as possible in the healthy vascular wall area without coinciding with any important vascular branchings. For example, the branchings of the renal arteries, of the superior mesenteric artery (e.g., arteria mesenterica superior), of the truncus c(o)eliacus, and of the internal iliac artery (e.g., arteria iliaca interna) are to be kept free. A sensitive point is the placement of the "main stent" in the aorta, during which the vascular branchings mentioned are not to be blocked. Even with relatively simple stents, which, for example, in addition to the aorta, merely encompass the femoral arteries, the final stent often is to be made up of a "main stent" and "part-stents". Thus, for stents for the femoral arteries, the common iliac arteries (e.g., arteriae iliacae communes) are normally "flange-mounted"

onto an aortic stent acting as a main stent, as is explained below based on FIG. 3. In more complex stents, known as fenestrated or branched stents, other part-stents are added as well. Methods for supporting these procedures using anatomically correct overlaying of, for example, presegmented CT data are being trialed and show the physician the aorta and branching vessels in the form of a permanent roadmap, as described, for example, in DE 10 2011 005 777 A1.

In order not to have to inject contrast agent for the permanent display of vessels for control purposes during the complex stent positioning, a reference image may be overlaid in an anatomically correct manner to assist with positioning. This shows the vessels (e.g., in the case according to FIG. 5, the aorta and branching vessels). This reference image may be either a 2D angiography (DSA) or a previously recorded 3D data set (e.g., a CT angiography) of the aneurysm. These show more details and may be overlaid using any angulations of the C-arm.

A problem with these overlays is that the reference image (2D or 3D) shows the vascular anatomy at a particular point in time. If, for example, the physician introduces very inflexible or rigid medical instruments (e.g., catheters), the anatomy of the vessels deforms. If this deformation is not corrected in the overlaid reference image, this produces an inaccuracy or "incongruity" in the overlay, as further explained below. This may result in uncertainties in the navigation during a subsequent intervention, in which the overlay serves as an aid to navigation.

DE 10 2010 012 621 A1 has already proposed a way of interoperatively correcting such deformations, in which the medical instrument is located or reconstructed from two X-ray projections.

This method for deformation equalization involves adaptation of a reference image, which automatically corrects displacements that may occur as a result of inserting medical instruments (e.g., when using a stent in an aorta). In this way, the displacements that may not initially be perceived in the image because of the angle of view may be corrected.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an angiographic examination method for depicting a target region inside a patient with a vascular system such that a three-dimensional correction facility is possible from just one projection image, with a considerably improved method sequence and radiation exposure for the patient is provided.

An examination method includes capturing a volume data set of the target region with the examination object, registering the volume data set to the C-arm, and extracting information about an assumed course of the examination object in the volume data set inside the target region. The method also includes generating at least one 2D projection image of a medical instrument inserted in the target region, which has a deviation between overlay and an actually projected instrument. The method includes 2D/3D merging of the at least one 2D projection image and the registered volume data set for generating a 2D overlay image, detecting the instrument inserted in the target region in the 2D overlay image with a first projection matrix, and generating a virtual 2D projection using a virtual projection matrix. The method includes 3D reconstructing the instrument, in which a 3D position of the instrument is determined from the two projections, and overlaying the 2D projection image and the virtual 2D projection and distorting at least one part of the 2D projection image such that the current and the assumed course of the vessels are brought into congruence.

Thanks to this 3D correction of the overlay images because the 3D position of the inserted instrument is identified from only one X-ray projection, the displacements arising because of the insertion of instruments may essentially be eliminated automatically.

In one embodiment, the generating of the virtual 2D projection includes generating a virtual projection matrix by rotating the first projection matrix by an angle ($\alpha$) of, for example, 90°, about the patient axis, generating a virtual projection of the instrument using the virtual projection matrix, and approximating the instrument in the virtual projection by estimating the position of the instrument from the projection.

In one embodiment, the 3D volume may be captured based on a previously performed CT angiography or a C-arm computed tomography recorded during the intervention.

The information about an assumed course of the examination object may be obtained using a 3D segmentation over the course of the vessels.

In one embodiment, the information may be the center lines of the vessels and/or the course of vascular lumina.

The detection of the instrument may produce a two-dimensional polygon line that corresponds to the position of the instrument in this projection.

In one embodiment, during the approximation of the instrument, a smoothing interpolation may be used to determine the position of the instrument, which depending on the assumed inflexibility of the instrument, is a linear, quadratic or more flexible spline interpolation.

A simple calculation of the 3D reconstruction of the instrument ensues if the calculation includes a triangulation from the two projections.

In one embodiment, for the overlay and distortion, a part of the vessel corresponding to the course of the vessel may be positioned so as to coincide with the relevant part of the inserted instrument for which 3D positions are available. The overlay of the 2D projection image and of the virtual 2D projection is adjusted depending on the position and penetration depth of the instrument.

DETAILED DESCRIPTION

Figure 1:
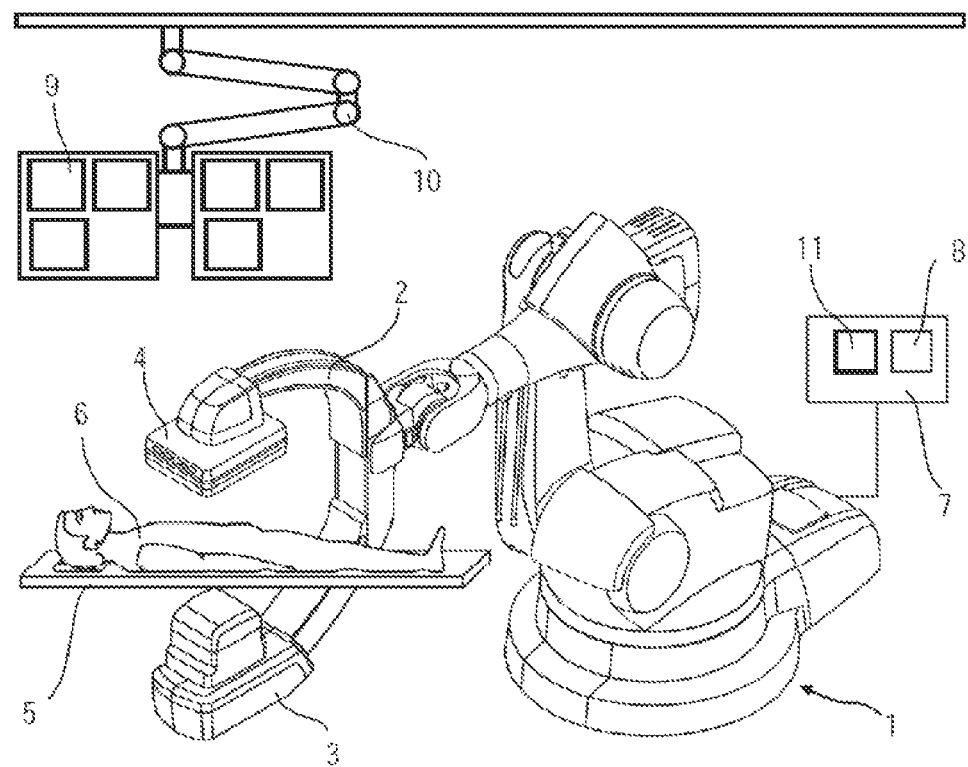
FIG. 1 shows a known C-arm angiography system with an industrial robot as a support apparatus.
Figure 2:
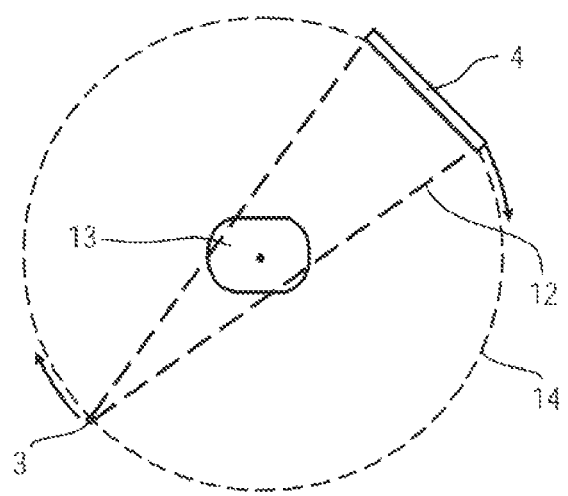
FIG. 2 shows a schematic representation of geometric relationships in rotational angiography using the C-arm angiography system of FIG. 1
Figure 3:
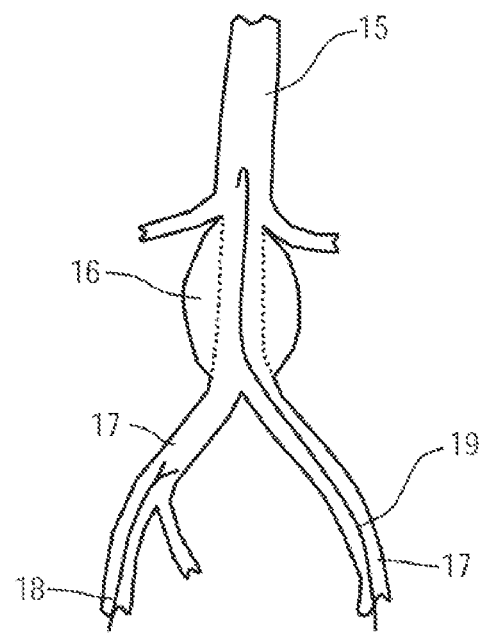
FIG. 3 shows an abdominal aorta with an aortic aneurysm.

FIG. 3 illustrates an abdominal aorta 15 that has an abdominal aortic aneurysm (AAA) 16. An AAA 16 is a vascular dilatation on the abdominal aorta 15. The aorta 15 branches into femoral arteries 17 (e.g., arteria iliaca communis).

Figure 4:
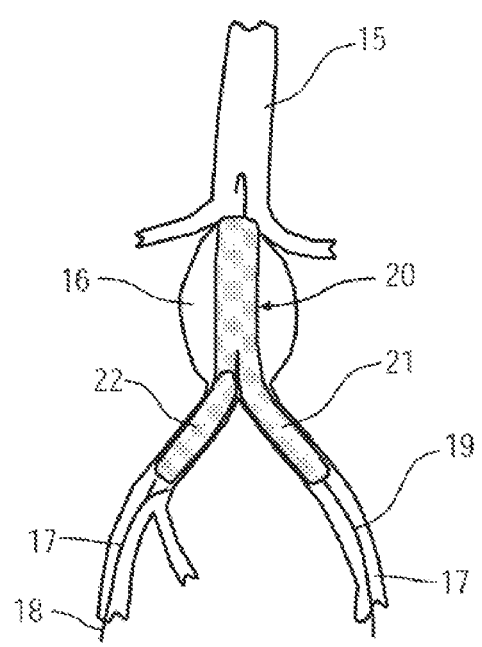
FIG. 4 shows the aorta of FIG. 3 with an inserted stent graph.

The aortic aneurysm 16 is treated by inserting a stent graft (e.g., a composite vascular stent), as illustrated in FIG. 4. Guide wires 18 and catheters 19, by which stent grafts 20 are inserted, are inserted into the aorta 15 through the femoral arteries 17 by way of both groins.

In the case of complex stent grafts 20 that also encompass the femoral arteries 17, a final stent may be composed of "part-stents." For example, an iliacal stent 22, as a part-stent for the other femoral artery 17, is to be "flange-mounted" onto an aortic stent 21 as a main stent, which projects through the AAA into one of the femoral arteries 17, through a so-called window.

Figure 5:
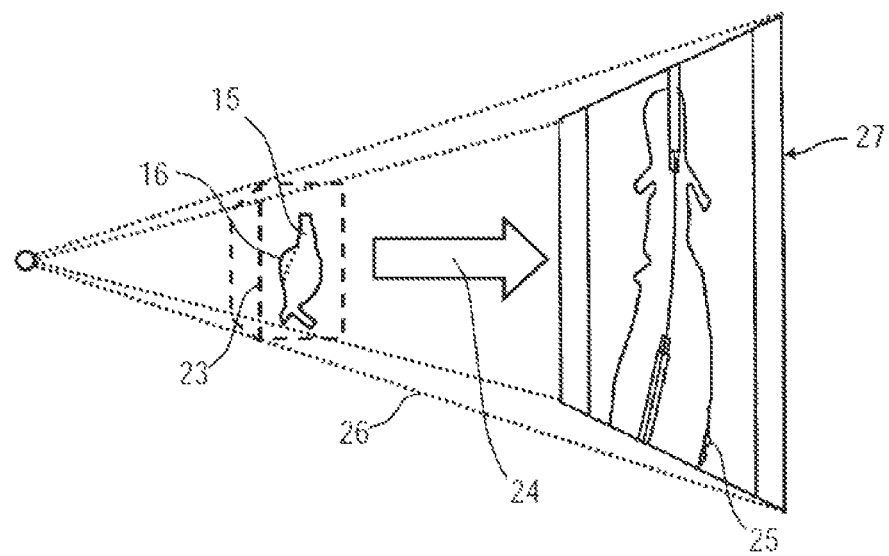
FIG. 5 shows an illustration to explain the principle of a 2D/3D overlay.
Figure 6:
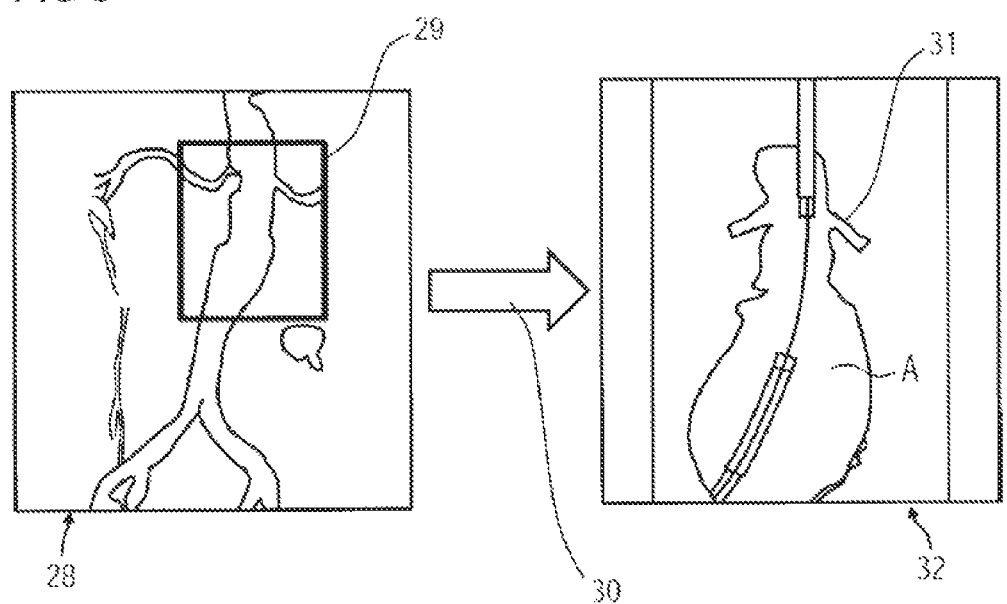
FIG. 6 shows an illustration to explain the principle of a 2D/2D overlay.
Figure 7:
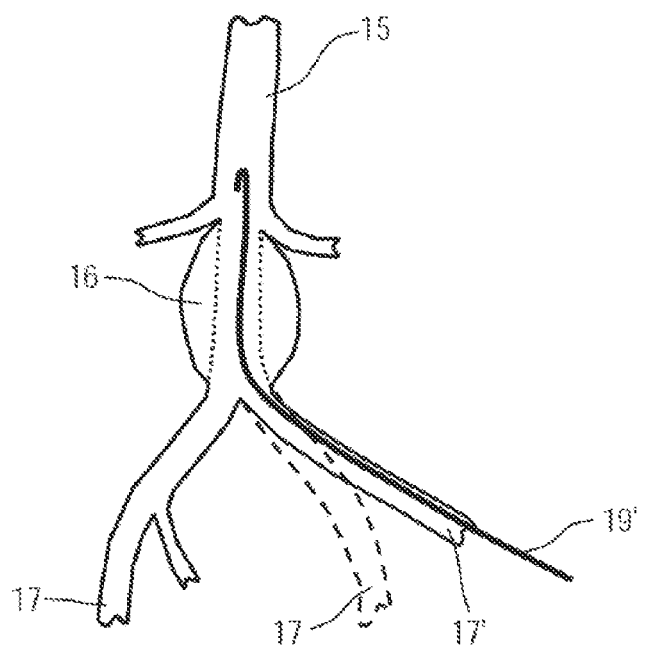
FIG. 7 shows a schematic illustration to explain vascular deformation during an intervention.

Based on FIGS. 5 and 6, the principle of a 2D/3D and a 2D/2D overlay are explained in more detail.

In order to provide the physician with additional information as assistance when inserting AAA stents, a previously recorded reference image is overlaid anatomically correctly over a current fluoroscopy image generated by a C-arm system 2 to 4. The reference image may be a 3D data set or volume data set of the aorta 15 with the abdominal aortic aneurysm 16 according to FIG. 4 (e.g., a presegmented preoperative computed tomography or rotational angiography using a C-arm angiography system).

FIG. 5 shows the overlay of a current fluoroscopy image with the pre-interventionally generated volume data set 23, which, for example, may be present as a 3D grating model, as depicted by way of example in the cube. The 3D grating model is mapped by 3D projection 24 into the fluoroscopy image as 2D segmentation 25, as symbolized by the dotted lines 26. A 2D/3D overlay image 27 is produced as a reference image.

In contrast, in FIG. 6, there is no volume data set 23 with 3D grating model, but only a 2D projection image 28 (e.g., an angiography). The abdominal aortic aneurysm 16 in a section 29 of the 2D projection image 28 is segmented. Using 2D projection 30, this 2D segmentation 31 is projected into the current fluoroscopy image (even if only from precisely this view), and a 2D/2D overlay image 32 is obtained as a reference image.

Although a one-off administration of contrast agent is to be provided for this 2D overlay using, for example, a digital subtraction angiography (DSA), the advantage compared to the "normal" roadmap is that certain changes in the C-arm system 2 to 4 such as zoom, source image distance (SID), and/or small movements of the patient positioning table with the tabletop 5 may be tracked.

In the case of FIGS. 5 and 6, only the outline of the 2D projection is ever illustrated, not the complete model.

The method acts to get from the 2D projection image 28 to the 2D/2D overlay image 32 are as follows. The aorta 15 with the abdominal aortic aneurysm 16 is segmented in the 2D projection image 28, and the outlines of the segmented aorta are superimposed as 2D segmentation 31 into the native fluoroscopy image of the 2D projection image 28, of the angiography.

Vascular Deformation During the Intervention

If now starting from the circumstances according to FIG. 3, a rigid or inflexible medical instrument 19' that may not be distorted by the vascular wall is inserted, for example, via a femoral artery 17. The vascular wall may in some cases deform to the femoral artery 17' to a greater or lesser extent.

Figure 8:
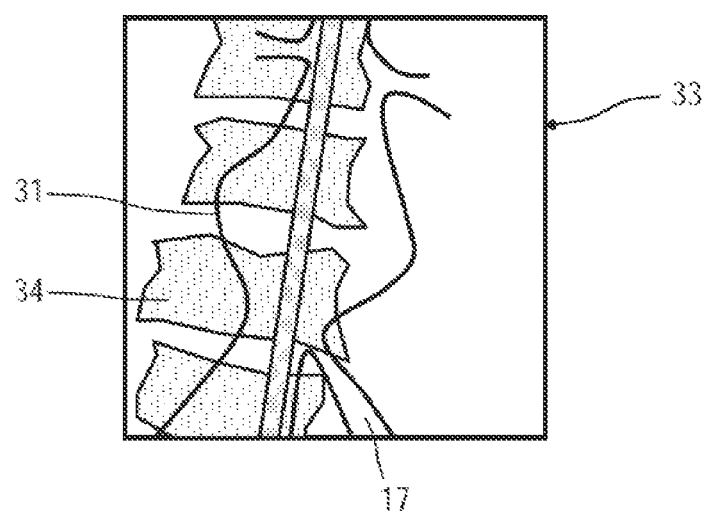
FIG. 8 shows a reference image as a basis for navigation by a physician.
Figure 9:
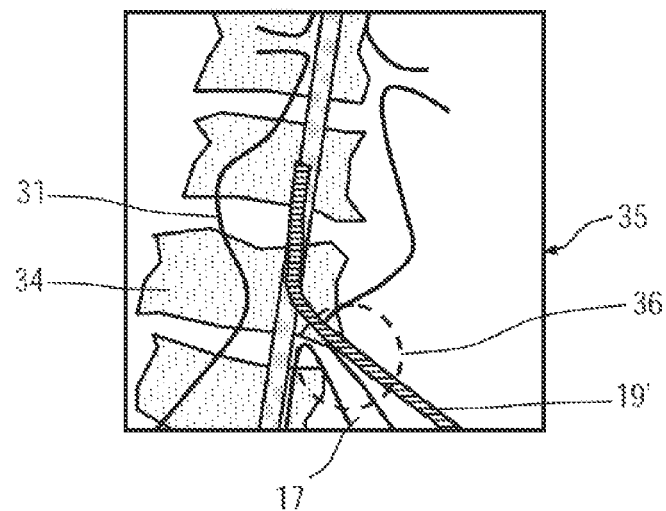
FIG. 9 shows a presegmented fluoroscopy image to explain the origin of an overlay error because of a deformation of an artery by an inflexible medical instrument.

If, starting from a reference image 33, as schematically illustrated in FIG. 8, with 2D segmentation 31 in front of a spinal column 34, in which the circumstances according to FIG. 3 are sketched, this vascular deformation caused by the inflexible medical instrument 19' is not corrected in the corresponding presegmented fluoroscopy image 35. An overlay error 36 is produced, as is schematically illustrated in FIG. 9. The overlay error 36 is based on an inaccuracy or an "incongruence" during the overlay that may lead to uncertainties during the following intervention, in which the overlay serves as a navigation aid. This overlay error 36 manifests in a virtual deviation of the mapping of the femoral artery 17 from the mapping of the rigid medical instrument 19' in the deformed femoral artery 17'.

Presegmentation of the Reference Volume

A presegmentation 37 of the reference volume with the aneurysm by automatic or user-assisted 2D or 3D image processing may be provided. In this case, for example, the surface 38 or the outline of the vessels and a course of the vessels may be determined in the form of the center line 39 of the vessels. This may happen both with the 2D reference image and with the 3D reference image. Medical instruments such as, for example, catheters or guide wires may be identified and tracked in 2D images. In this case, a partially flexible 2D/3D or 3D/3D registration may be provided (e.g., of 2D and 3D angiographies).

Figure 11:
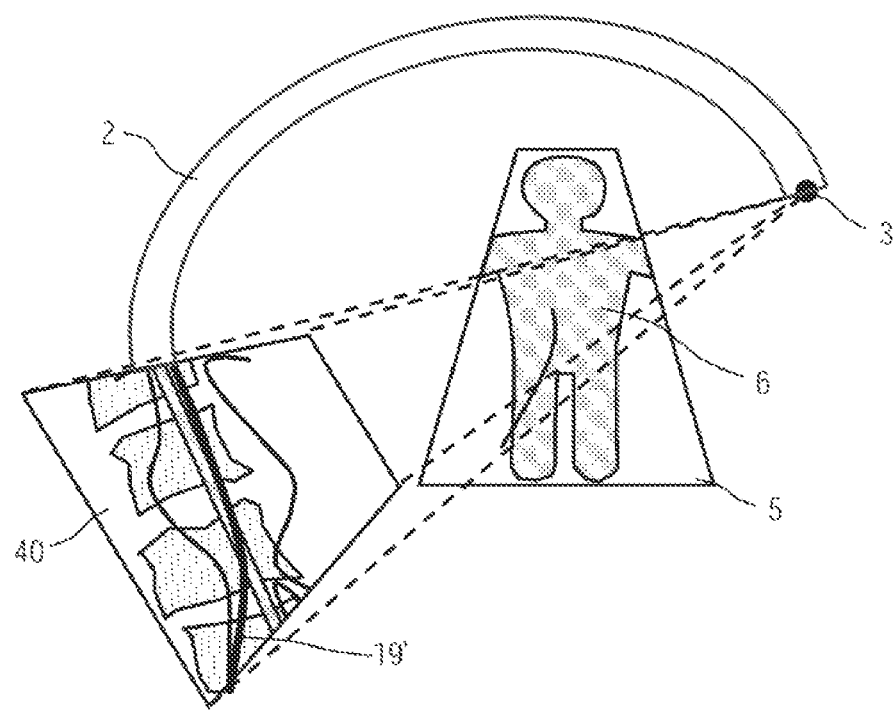
FIG. 11 shows an initial situation for the generation of a projection matrix for a fluoroscopy image from a particular angulation of the C-arm.

FIG. 11 illustrates an initial situation for generating a projection matrix for a fluoroscopy image, in which a fluoroscopy image 40 of the patient 6 with an inserted medical instrument 19' who is lying on the tabletop 5 of the patient positioning couch is generated from a particular angulation of the C-arm 2.

Generation of a Virtual Projection Matrix PM2

The C-arm projection according to FIG. 11, which maps the object (e.g., the patient 6) as a fluoroscopy image 40, may be described using a projection matrix PM1. By rotating by a particular predetermined angle α, a projection matrix PM2 (e.g., a virtual projection matrix), based on which the object may be projected (e.g., virtually projected) from a different angulation, may be calculated.

Figure 12:
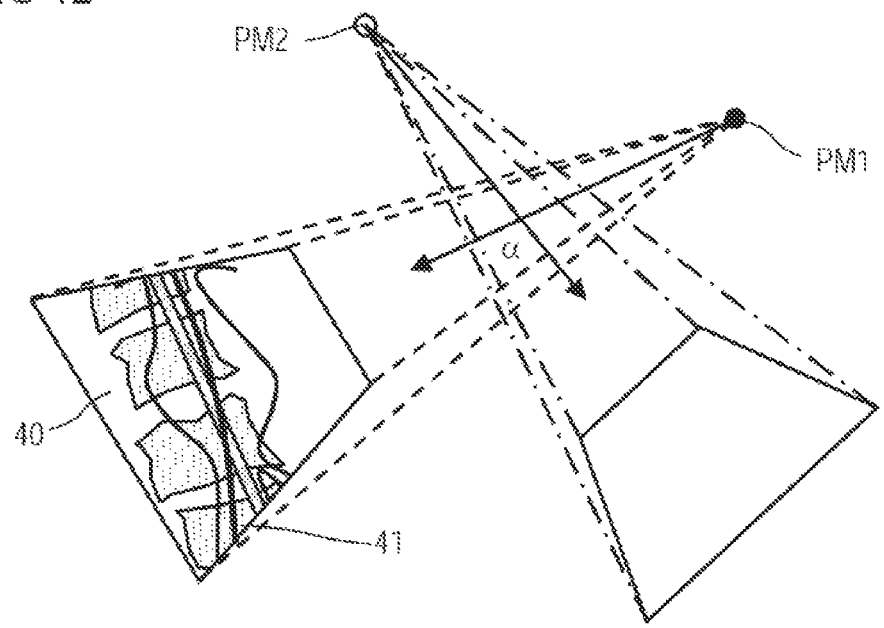
FIG. 12 shows generation of a virtual projection matrix.

In the fluoroscopy image 40, the projected medical instrument 19' may be segmented and represented as a polygon line 41, as shown in FIG. 12.

Virtual Projection 42

Figure 13:
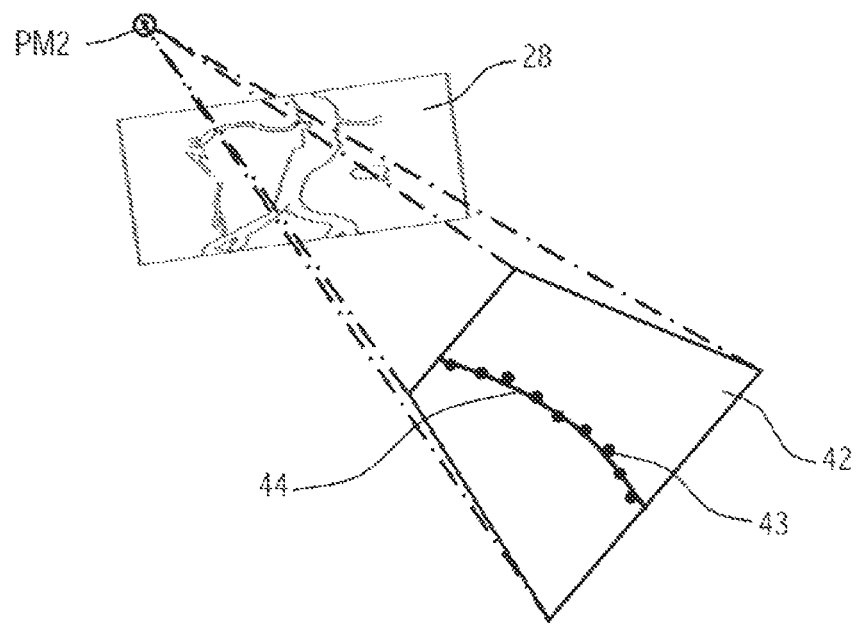
FIG. 13 shows a virtual projection.

Based on FIG. 13, it is shown how, with the help of the virtual projection matrix PM2, the polygon line 41 is projected as a two-dimensional point set of a virtual center line 43 of the vessels in which the instrument 19' to be reconstructed is located. This produces a virtual projection 42. The center lines 43 are interpolated (e.g., quadratically) and produce a second, virtual projection of the instrument as a virtual polygon line 44.

Reconstruction of the Medical Instrument

Figure 14:
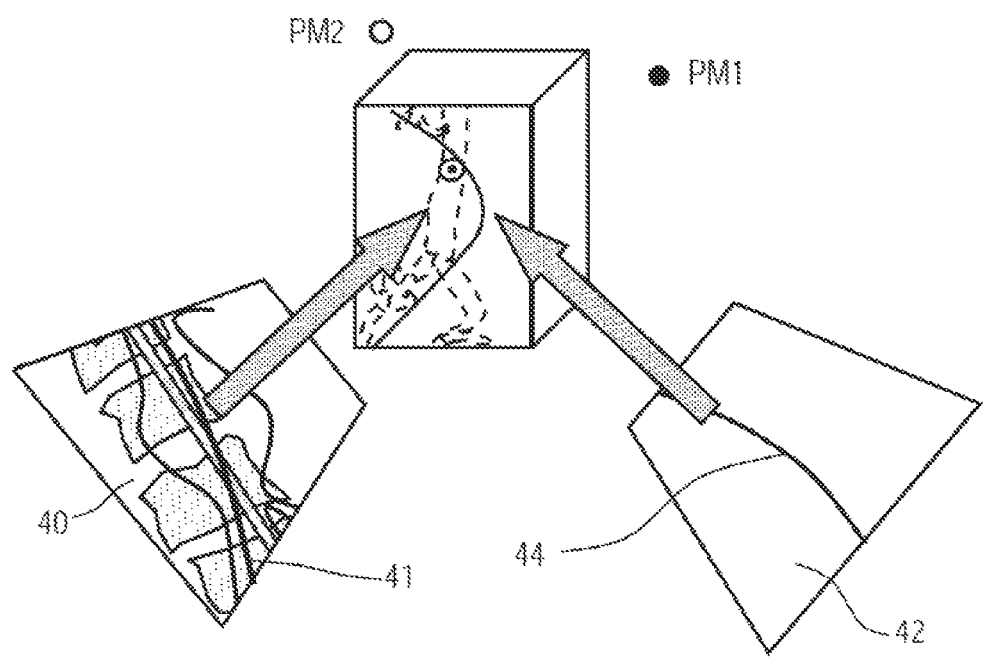
FIG. 14 shows a reconstruction of a medical instrument from the fluoroscopy image and the virtual projection.

The medical instrument may be reconstructed in 3D using the two polygon lines (e.g., the polygon line 41 that corresponds to the actual projection of the instrument and the virtual polygon line 44 that corresponds to the estimated, virtual projection of the instrument) with the projection matrices PM1 and PM2, as is demonstrated in FIG. 14.

Principle of the Proposed Correction in the Image Plane

Figure 15:
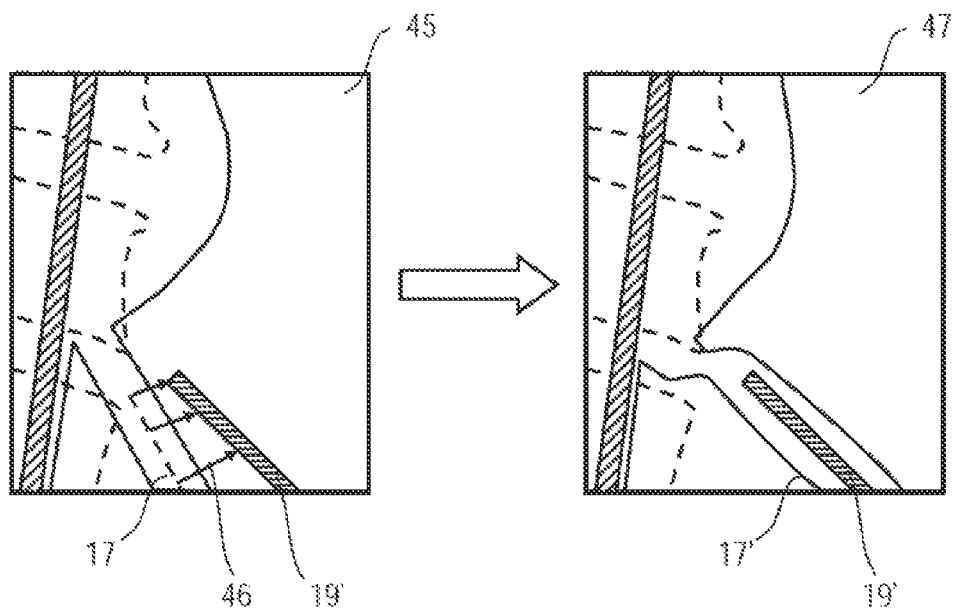
FIG. 15 shows an exemplary proposed correction in the image plane.
Figure 16:
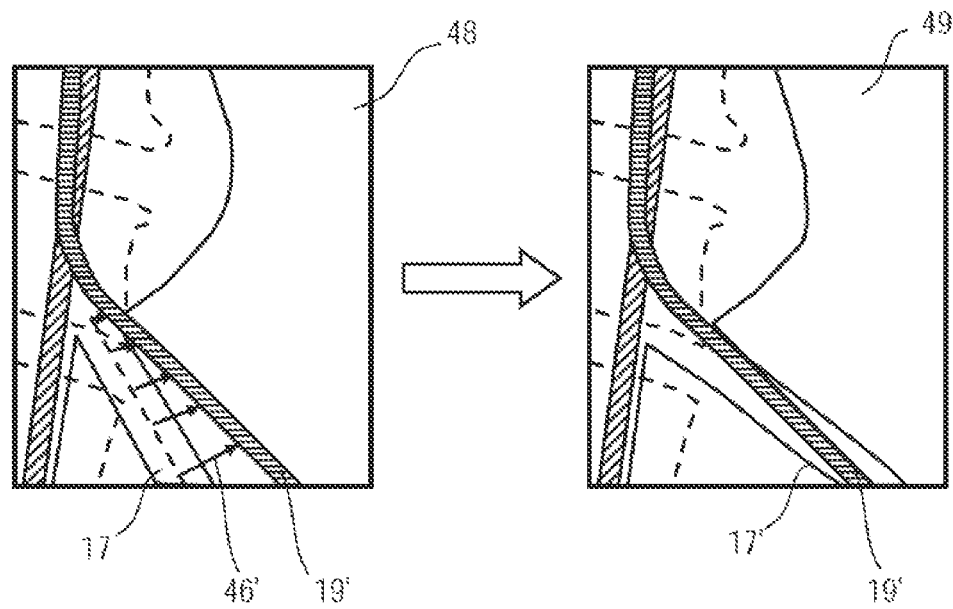
FIG. 16 shows an exemplary correction in the image plane with a greater penetration depth of the medical instrument.

This proposed correction is explained in more detail in the image plane based on FIGS. 15 and 16. A reference image 45 that shows the status before the insertion of the medical instrument 19(') is overlaid with the actual position and location of the inserted medical instrument 19', as identified by automatic image processing or a position sensor. This indicates the current course of the vessel (e.g., the deformed femoral artery 17'). The reference image 45 (e.g., the center line 39 of the segmentation 25) is then distorted according to the displacements 46, so that the current and the assumed course of the deformed femoral artery 17' are again congruent, as is represented in the distorted reference image 47.

FIGS. 15 and 16 illustrate, for example, situations that show the principle of medical instruments 19' being inserted by different distances. The overlay, distortion and displacement 46' in the reference image 48 are adjusted differently depending on the position and penetration depth of the medical instrument 19', as the distorted reference image 49, in which the whole visible femoral artery 17' is deformed, shows. As a result, however, the courses of the femoral artery 17' and of the medical instrument 19' are again congruent.

Figure 17:
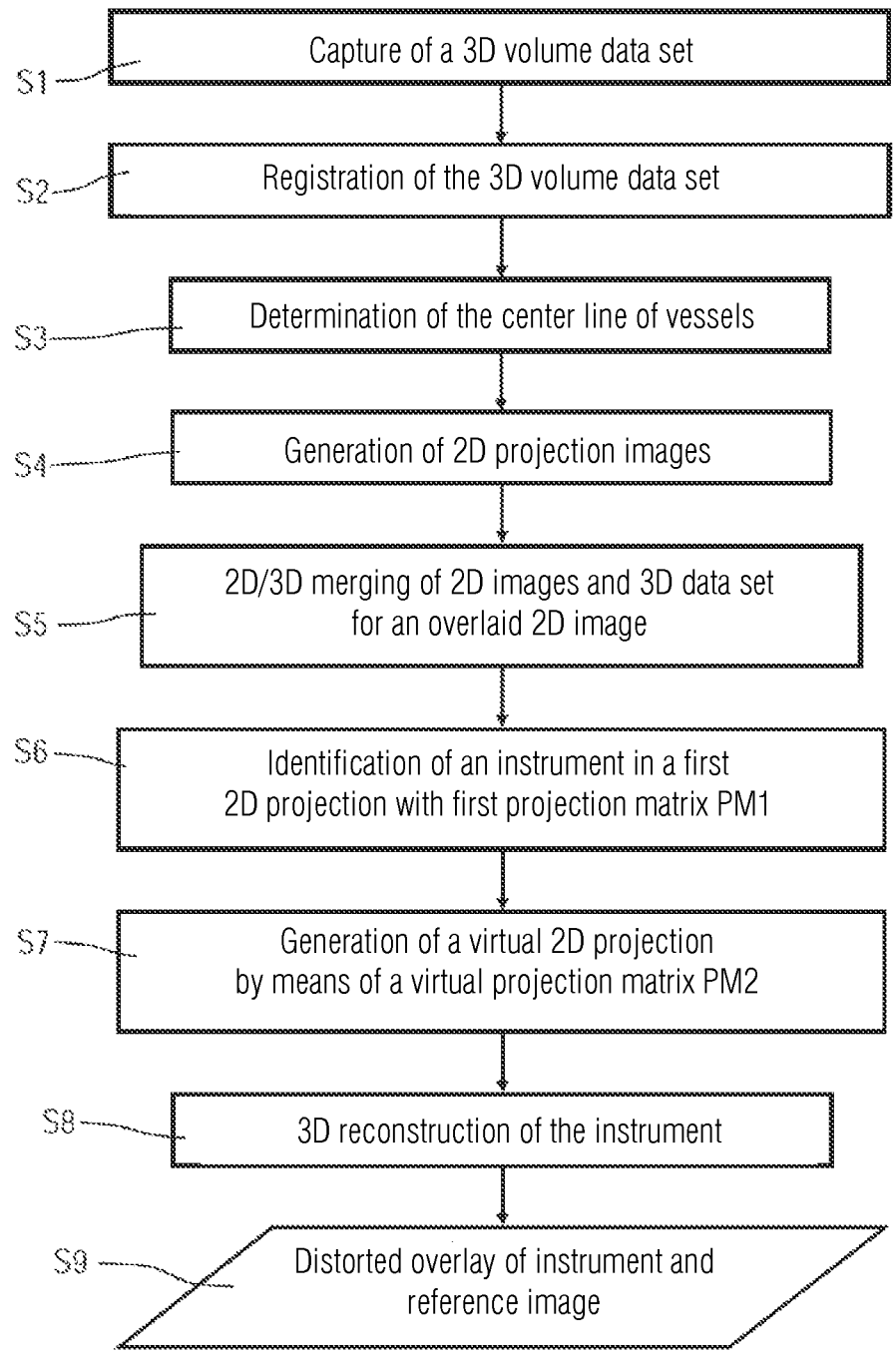
FIG. 17 shows a flow chart of one embodiment of a method.

Based on FIG. 17, the method sequence of the method of one or more of the present embodiments is explained in more detail. According to act S1, a volume data set 23 of the target region or of the examination object 15 and 17 is captured and stored. The capture may be achieved, for example, by a computed tomography system or C-arm computed tomography system (e.g., in accordance with the DynaCT method).

In act S2, the volume data set 23 is registered to the C-arm 2.

A determination of the center line 39 according to act S3 is achieved by extracting information about an assumed course of the examination object 15, 17 in the volume data set 23 inside the target region.

From this volume data set 23, according to act S4, at least one 2D projection image 28 of a medical instrument 18, 19, 19' inserted in the target region is generated from a suitable C-arm angulation.

According to act S5, a 2D/3D merger of the at least one 2D projection image 28 and of the registered volume data set 23 is provided in order to generate a 2D overlay image 27, 32.

In act S6, by detecting the medical instrument 18, 19, 19' inserted in the target region in a first 2D projection (e.g., the fluoroscopy image 40) using a first projection matrix PM1 (e.g., in the 2D overlay image), the course of the medical instrument 18, 19, 19' is, for example, identified.

According to act S7, a virtual 2D projection 42 is generated by a virtual second projection matrix PM2 by rotating the first 2D projection by a particular predetermined angle α, and an approximation of the instrument 18, 19, 19' is performed in a virtual 2D projection 42.

In act S8, a 3D reconstruction of the instrument 18, 19, 19', in which the 3D position of the medical instrument is determined from the 2D identification under the projection PM1 (e.g., the polygon line 41) and from the approximation from the virtual projection PM2 (e.g., the virtual polygon line 44), is provided by triangulation from the two projections 40 and 42.

In act S9, the reconstructed instrument 18, 19, 19' is overlaid with the reference images 45 and 48. At least a part of the reference images 45 and 48 is subjected to distortions 46 and 46' such that the current and assumed course of the vessels are made to be congruent. In this case, at least a part of the vessel 17' that corresponds to the course of the vessel is made to coincide with the respective part of the inserted instrument 19', for which the position information is available. The overlays and distortions 46, 46' of the reference images 45 and 48 are adjusted depending on the position and penetration depth of the instrument 19', so that the distorted X-ray images 47 and 49 are obtained.

Figure 18:
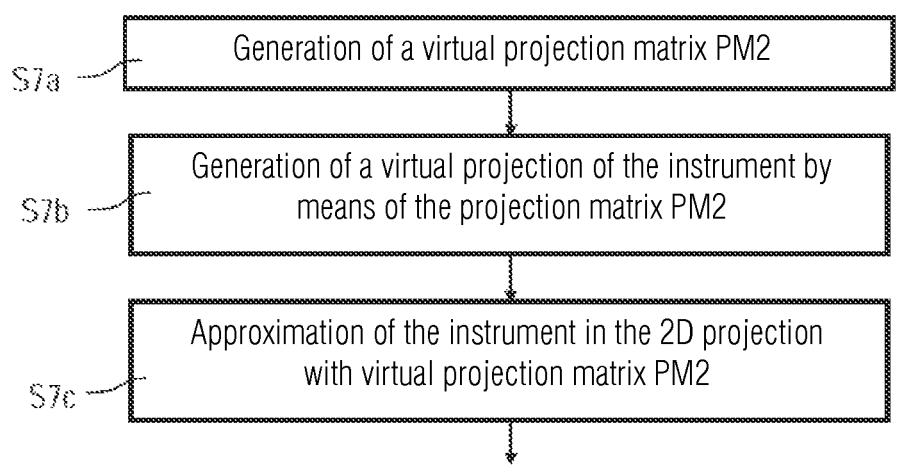
FIG. 18 shows a flow chart of one embodiment of a subdivided method act of FIG. 17.

FIG. 18 illustrates act S7 in more detail. In subact S7a, the virtual second projection matrix PM2 is first generated.

According to subact S7b, a virtual projection 42 of the instrument 19' is generated by the virtual projection matrix PM2.

In subact S7c, an approximation of the inserted instrument 19' is performed in the virtual projection 42. This approximation may serve as the basis for the 3D reconstruction of the instrument 19'.

Figure 19:
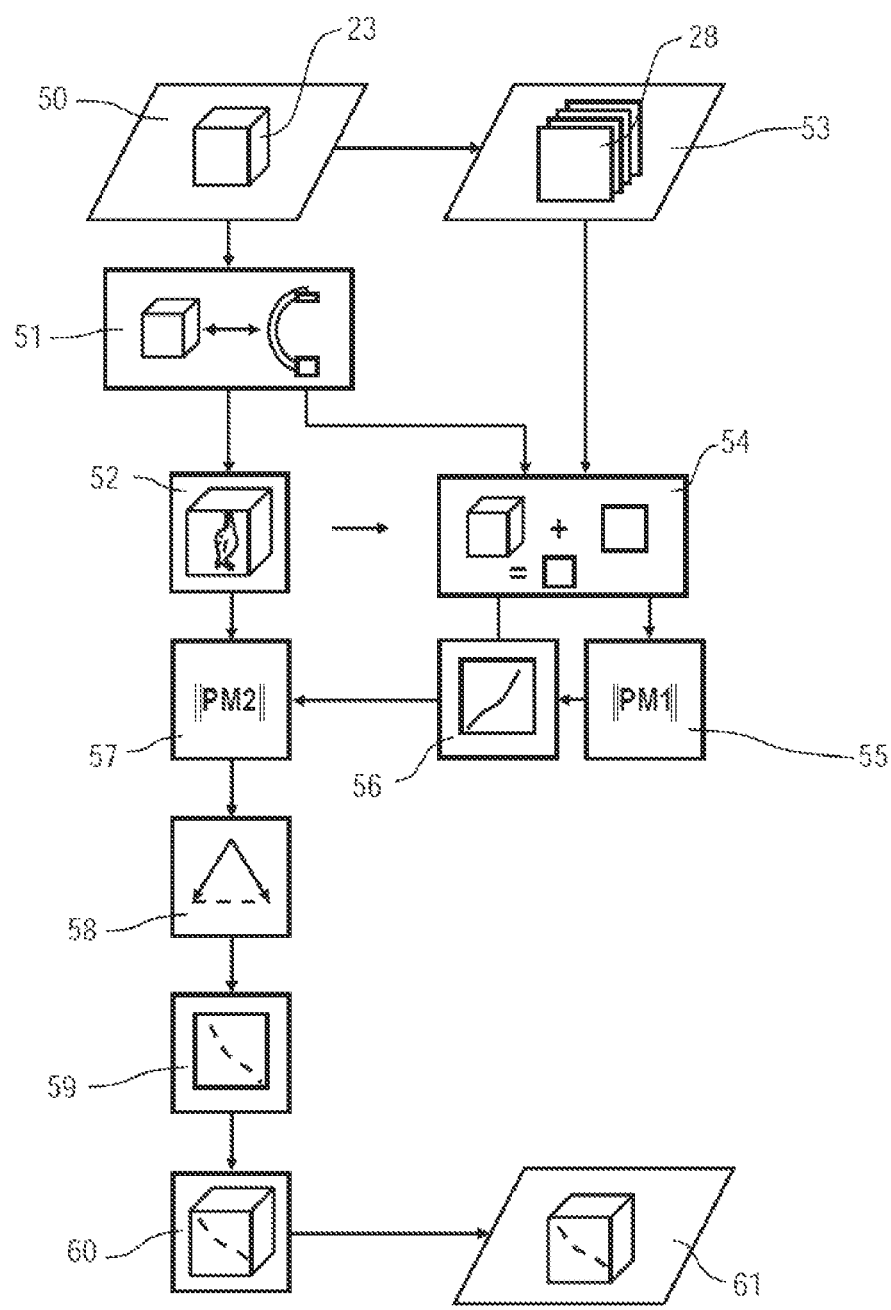
FIG. 19 shows a flow chart of one embodiment of the method sequence of FIGS. 17 and 18.

FIG. 19 shows a flow chart of one embodiment of the complete method sequence according to FIGS. 17 and 18, based on which the individual method acts and the sequence thereof may be better followed.

A capture 50 of a 3D volume data set 23 of the target region or of the examination object 15 and 17 is achieved, for example, by a CT angiography performed before an intervention or a C-arm computed tomography recorded during the intervention (e.g., in accordance with the DynaCT method).

In act 51, the 3D volume data set 23 is registered to the C-arm 2.

From this registered 3D volume data set 23, information about an assumed course of the examination object 15, 17 in the volume data set 23 inside the target region is determined by extraction 52 of the center line 39 of the vessels.

From the 3D volume data set 23, 2D projection images 28 of a medical instrument 18, 19, 19' inserted in the target region are generated 53 under a suitable C-arm angulation.

A 2D/3D merger 54 of the 2D projection images 28 and of the registered volume data set 23 is provided in order to generate 2D overlay images 27, 32.

From this data, a first projection matrix PM1 is derived 55.

The course of the medical instrument is extracted by detecting 56 the medical instrument 18, 19, 19' inserted in the target region in a first 2D projection with a first projection matrix PM1.

By rotation about a particular predetermined angle α, a second projection matrix PM2 (e.g., a virtual projection matrix) is generated 57.

Using the virtual projection matrix PM2, a virtual projection 42 of the instrument 19' is generated 58.

In this virtual projection 42, the inserted medical instrument 18, 19, 19' is detected by approximation 59.

Following the detection of the instrument 18, 19, 19', a 3D reconstruction 60 of the instrument 18, 19, 19' takes place, whereby at least a part of the reference image 45 and 48 is subjected to distortions 46 and 46' such that the current and the assumed course of the vessels are made to be congruent. In this case, a part of the vessel 17' corresponding to the course of the vessel is made to coincide with the relevant part of the inserted instrument 19', for which the position information is available. The overlays and distortions 46 of the reference images 45 and 48 are adjusted depending on the position and penetration depth of the instrument 19', so that the distorted X-ray images 47 and 49 are obtained.

This 3D reconstruction 60 may, for example, be displayed 61 on a display of the monitor bracket 9.

The principle of correction based on the repair of an aortic aneurysm is described in summary below in an exemplary embodiment.

Figure 10:
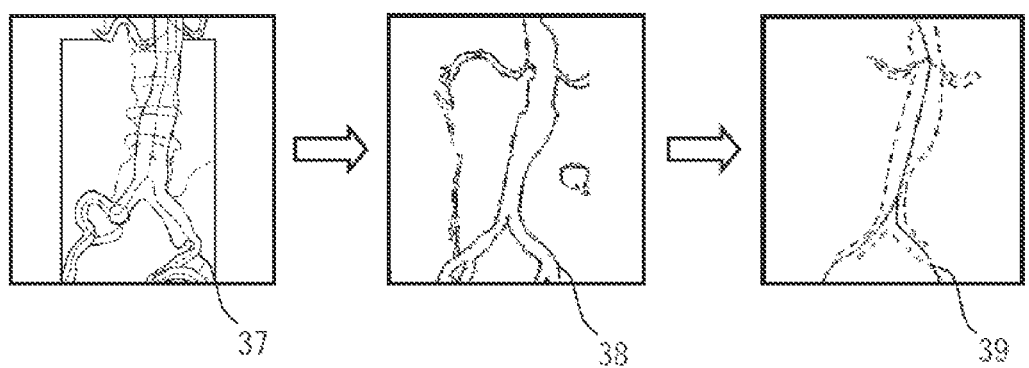
FIG. 10 shows a presegmentation of the reference volume.

Basic preconditions for the method of one or more of the present embodiments include a 3D volume (e.g., a previously performed CT angiography or a C-arm CT such as Siemens DynaCT®) that is registered to the C-arm (or to the relevant fluoroscopy images) being recorded during the intervention. Information (e.g., about a semi-automatic or automatic 3D segmentation, depending on the data set used) over the course of the vessels (e.g., the center lines of the vessels and/or the course of vascular lumina and/or other corresponding information (see FIG. 10)) is provided. A facility to identify and track inserted medical instruments (e.g., the instrument for inserting stents) is provided. This may happen, for example, via corresponding identification or tracking of the medical instruments in the 2D fluoroscopy images.

One or more of the present embodiments relate to the 3D reconstruction of a medical instrument inserted into the vessel under the aforementioned preconditions from just one X-ray projection.

The method includes X-ray projection of the instrument or device. During the intervention, fluoroscopy of the patient 6, for example, with an inserted medical instrument 19' takes place from a suitable C-arm angulation, in which a deviation between overlay of the reference image and an actually projected instrument is established, as has already been explained based on FIG. 9.

The medical instrument is identified in a first 2D X-ray projection with a first projection matrix. The result of this detection of the medical instrument 19' in the first 2D X-ray projection with a first projection matrix PM1 is a two-dimensional polygon line 41 that corresponds to the position of the medical instrument 19' in this projection (e.g., the fluoroscopy image 40).

A "virtual" second 2D X-ray projection is generated with the help of a virtual projection matrix PM2. With the generation of the second virtual projection matrix PM2, a projection matrix is basically composed of intrinsic parameters (e.g., pixel size, etc.) and extrinsic parameters (e.g., translation and rotation of the projected 3D object). For the virtual second projection matrix PM2, any intrinsic parameters may be assumed or, for simplicity's sake, the parameters that also apply for the first projection matrix PM1. The extrinsic parameters are selected such that the rotation by a sufficiently large angle differs from the first projection matrix PM1 (e.g., by a rotation by 90° about the patient axis). The registered object is projected virtually by the second projection matrix PM2 from a different side.

A virtual second projection 42 is generated. From the registered reference volume, the center line of the vessels that contain the instrument 19' to be reconstructed are forward-projected using the virtual second projection matrix PM2. In the case of an aortic aneurysm 16, this would, for example, be the center line 39 of the aorta 15 and of the femoral artery (e.g., the deformed femoral artery 17') to be corrected. The result is a two-dimensional point set of the virtual center line 43, which corresponds to the projections of the center lines.

The medical instrument is approximated in the virtual second projection. From the projected points of the virtual center line 43, the position of the medical instrument 19' is estimated from the virtual projection 42 of the virtual second projection matrix PM2. Assuming that the inserted instrument 19' is located basically in the corresponding vessels 17, a smoothing interpolation of the center line projection is assumed as the position of the instrument. Depending on the assumed inflexibility of the medical instrument 19', this may be a linear, quadratic or more flexible spline interpolation. The result is a two-dimensional polygon line that corresponds to the estimated position of the medical instrument 19'.

The medical instrument is 3D reconstructed. The 3D position of the medical instrument is determined as a reconstruction of the 2D identification under the projection PM1 (e.g., the polygon line 41) and from the approximation from the virtual projection PM2 (e.g., the virtual polygon line 44) by triangulation from two projections 40 and 42.

The assumptions for the correction are then the same, as described, for example, in DE 10 2010 012 621 A1, and are listed here once again for the sake of completeness. The position identified in the fluoroscopy image 40 indicates the current course of the vessel 17, since the medical instrument 19' is located inside the vessel 17. The reference image 45 or the center line of the segmentation of the reference image 45 is correspondingly distorted by displacements 46 and 46', such that the current and the assumed course of the vessel are again congruent. The corresponding part of the vessel 17' is made to coincide with the respective part of the identified medical instrument 19' (FIG. 15). The overlay of the reference image 45, 48 is adjusted differently depending on the position and penetration depth of the instrument 19' (see FIGS. 15 and 16). The remainder of the course of the vessel (i.e., the part into which no medical instrument has yet been inserted) is extrapolated, for example, on the assumption of "smoothness conditions," since vessels do not generally bend sharply or anything similar. In this case, regions far removed from the identified instrument 19' are, for example, not deformed at all (e.g., the renal arteries) if an instrument 19' is inserted into the femoral arteries 17, 17', more specifically such that a smooth course of the vessels without discontinuities or breaks is maintained.

Other embodiments may be provided optionally or alternatively. Alternatively to the above-described precondition 2, the information about the course of the vessels (e.g., 2D or 3D) may also be defined manually by the user (e.g., drawn in) and may also be given by a mathematical description (e.g., a high-degree polynomial or another suitable function). The adjustment of the overlay may take place, for example, by adjusting the functional parameters depending on the position of the identified instrument.

Alternatively to the above-described precondition 3, the position of the inserted instrument may also be defined manually by the user (e.g., drawn in).

Not just one but several instruments may be identified or tracked. Thus, for example, other stationary instruments (e.g., guide wires inserted into the renal arteries) may be identified and tracked in order to provide that the overlays are congruent at several points.

Generally, the method may be extended to all procedures that profit from the overlay, where appropriate, of presegmented reference images (e.g., including when replacing aortic valves, interventions in coronary vessels, etc.).

Due to the correction of overlaid reference images (e.g., for the stents in an aorta), displacements that arise from the insertion of instruments are corrected essentially automatically. For example, using the 3D correction of one or more of the present embodiments, the 3D position of the inserted instrument may be determined from just one X-ray projection.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An angiographic examination method for depicting a target region inside a patient with a vascular system as an examination object using an angiography system comprising an X-ray emitter and an X-ray image detector that are attached to ends of a C-arm, a patient positioning couch with a tabletop on which the patient is positioned, a processor, an image system, and a monitor, the angiographic examination method comprising:
    capturing a volume data set of the target region with the examination object;
    registering the volume data set to the C-arm;
    extracting information about an assumed course of the examination object in the volume data set inside the target region;
    generating at least one two-dimensional (2D) projection image of a medical instrument inserted in the target region;
    generating a 2D overlay image, the generating of the 2D overlay image comprising 2D/3D merging of the at least one 2D projection image and of the registered volume data set;
    detecting the medical instrument inserted in the target region in the 2D overlay image with a first projection matrix;
    generating a virtual 2D projection of the medical instrument using a virtual projection matrix, wherein the virtual projection matrix is based on the first projection matrix;
    reconstructing the medical instrument in three dimensions, in which a three-dimensional (3D) position of the medical instrument is determined from the virtual 2D projection and the at least one 2D projection image of the medical instrument; and
    overlaying the virtual 2D projection and the at least one 2D projection image of the medical instrument, and distorting a center line of at least a part of the at least one 2D projection image by a displacement such that a current course and the assumed course of the vessels are congruent.

2. The angiographic examination method of claim 1, wherein generating the virtual 2D projection of the medical instrument comprises:
    generating a virtual projection matrix, the generating of the virtual projection matrix comprising rotating the first projection matrix by an angle about an axis through the patient;
    generating the virtual 2D projection of the medical instrument using the virtual projection matrix; and
    approximating the medical instrument in the virtual 2D projection of the medical instrument, the approximating comprising estimating the position of the medical instrument from the virtual 2D projection of the medical instrument.

3. The angiographic examination method of claim 1, wherein capturing the volume data set comprises capturing a 3-D volume based on a previously performed computed tomography (CT) angiography or a C-arm CT recorded during an intervention.

4. The angiographic examination method of claim 1, wherein the information about the assumed course of the examination object is obtained using a 3D segmentation over the course of the vessels.

5. The angiographic examination method of claim 4, wherein the information is center lines of the vessels, a course of vascular lumina, or the center lines of the vessels and the course of vascular lumina.

6. The angiographic examination method of claim 1, wherein detecting the medical instrument comprises generating a two-dimensional polygon line that corresponds to the position of the instrument in the at least one 2D projection image.

7. The angiographic examination method of claim 2, wherein the angle is 90°.

8. The angiographic examination method of claim 2, wherein during the approximating of the medical instrument, a smoothing interpolation is used to determine the position of the medical instrument, which depending on a level of inflexibility of the medical instrument, is a linear, quadratic or spline interpolation.

9. The angiographic examination method of claim 1, wherein reconstructing the medical instrument in three dimensions comprises a triangulation from the virtual 2D projection and the at least one 2D projection image of the medical instrument.

10. The angiographic examination method of claim 1, wherein the overlaying and distorting comprises positioning a part of the vessels corresponding to the course of the vessels so as to coincide with a relevant part of the inserted medical instrument for which 3D positions are available, and adjusting the overlay of the virtual 2D projection and the at least one 2D projection image of the medical instrument depending on the position and a penetration depth of the medical instrument.

11. The angiographic examination method of claim 2, wherein capturing the volume data set comprises capturing a 3-D volume based on a previously performed computed tomography (CT) angiography or a C-arm CT recorded during an intervention.

12. The angiographic examination method of claim 11, wherein the information about the assumed course of the examination object is obtained using a 3D segmentation over the course of the vessels.

13. The angiographic examination method of claim 12, wherein the information is center lines of the vessels, a course of vascular lumina, or the center lines of the vessels and the course of vascular lumina.

14. The angiographic examination method of claim 13, wherein detecting the medical instrument comprises generating a two-dimensional polygon line that corresponds to the position of the instrument in the at least one 2D projection image.

15. The angiographic examination method of claim 14, wherein the angle is 90°.

16. The angiographic examination method of claim 15, wherein during the approximating of the medical instrument, a smoothing interpolation is used to determine the position of the medical instrument, which depending on a level of inflexibility of the medical instrument, is a linear, quadratic or spline interpolation.

17. The angiographic examination method of claim 7, wherein reconstructing the medical instrument in three dimensions comprises a triangulation from the virtual 2D projection and the at least one 2D projection image of the medical instrument.

18. The angiographic examination method of claim 8, wherein reconstructing the medical instrument in three dimensions comprises a triangulation from the virtual 2D projection and the at least one 2D projection image of the medical instrument.

19. The angiographic examination method of claim 7, wherein the overlaying and distorting comprises positioning a part of the vessels corresponding to the course of the vessels so as to coincide with a relevant part of the inserted medical instrument for which 3D positions are available, and adjusting the overlay of the virtual 2D projection and the at least one 2D projection image of the medical instrument depending on the position and a penetration depth of the medical instrument.

20. The angiographic examination method of claim 8, wherein the overlaying and distorting comprises positioning a part of the vessels corresponding to the course of the vessels so as to coincide with a relevant part of the inserted medical instrument for which 3D positions are available, and adjusting the overlay of the virtual 2D projection and the at least one 2D projection image of the medical instrument depending on the position and a penetration depth of the medical instrument.

\* \* \* \* \*